United States Patent [19]

Skaletsky et al.

[11] Patent Number: 5,246,831
[45] Date of Patent: Sep. 21, 1993

[54] FELINE INFECTIOUS PERITONITIS VIRUS TEST UTILIZING MONOCLONAL IDIOTYPIC AND ANTI-IDIOTYPIC ANTIBODIES

[75] Inventors: Eileen Skaletsky, San Diego; Curtis N. Sharon, LaMesa, both of Calif.; Elizabeth A. Oseid, Maplewood, Minn.

[73] Assignee: Synbiotics Corporation, San Diego, Calif.

[21] Appl. No.: 736,513

[22] Filed: Jul. 26, 1991

Related U.S. Application Data

[63] Continuation-in-part of Ser. No. 586,207, Sep. 21, 1990, abandoned.

[51] Int. Cl.⁵ .............................................. C12Q 1/70
[52] U.S. Cl. ...................................... 435/5; 435/7.93; 435/7.94; 435/172.2; 435/240.27; 436/518; 436/547; 436/548; 530/387.2; 530/388.3

[58] Field of Search ............ 435/5, 7.93, 7.94, 240.27, 435/172.2, 965, 975; 436/518, 547, 548; 530/387.2, 388.3

[56] References Cited

PUBLICATIONS

Fiscus et al., J. Clin. Microbiology 22(3): 395-401, 1985.
Fiscus et al., J. Clin. Microbiology 25(8): 1529-1534, 1987.

*Primary Examiner*—Esther L. Kepplinger
*Assistant Examiner*—Donna C. Wortman
*Attorney, Agent, or Firm*—Edward S. Irons

[57] ABSTRACT

This invention provides (a) novel hybridoma cell lines which produce a monoclonal idiotypic antibody designated 1030.2.3.1 that binds an antigenic determinant present on FIPV but absent on FeCV; and (b) monoclonal anti-idiotypic antibodies designated 2814.6 and 2848.6 that mimic epitopes of this FIPV specific determinant.

Assay procedures and kits for use in such procedures to distinguish between FIPV and FeCV are described.

21 Claims, 1 Drawing Sheet

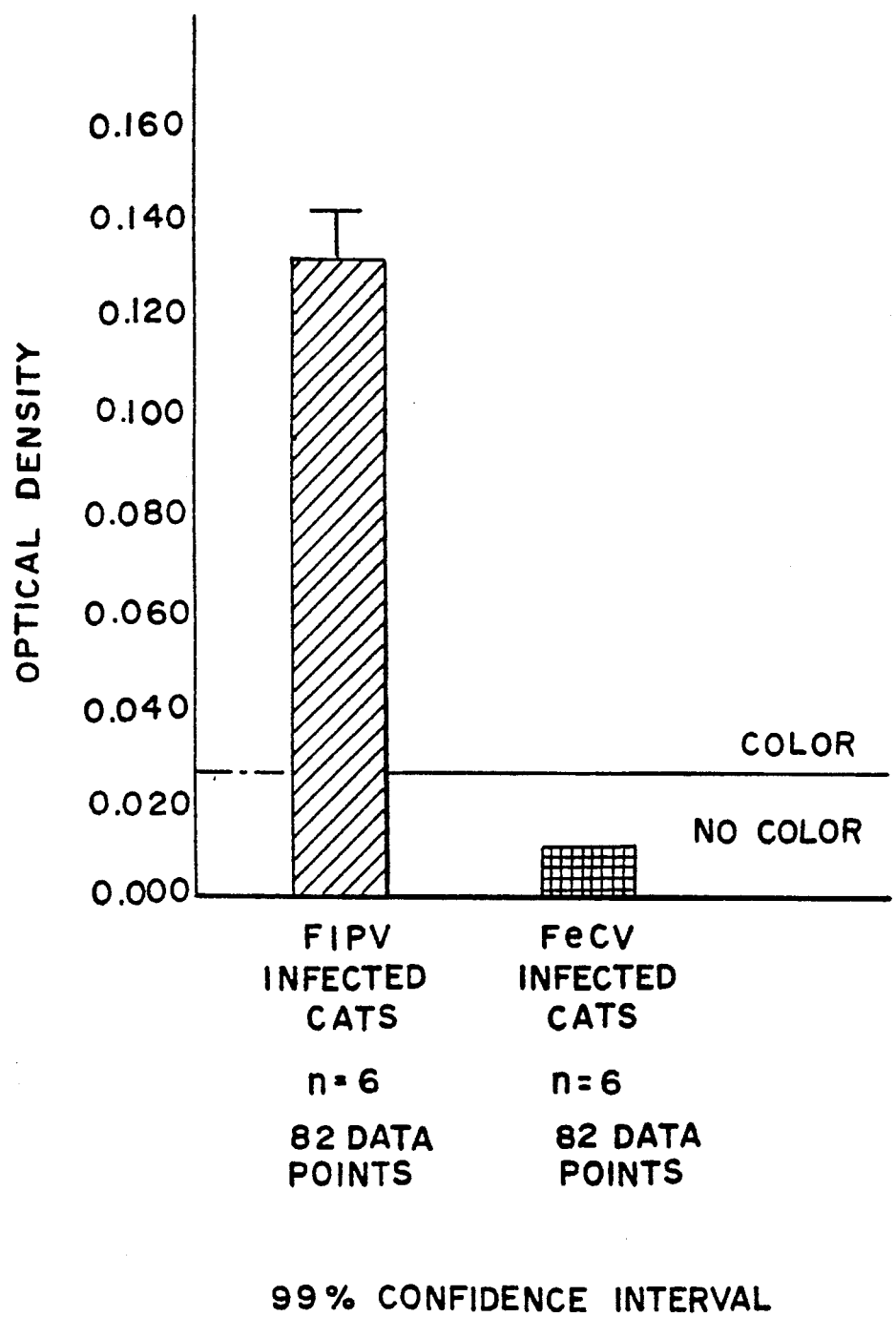

FELINE INFECTIOUS PERITONITIS VIRUS TEST UTILIZING MONOCLONAL IDIOTYPIC AND ANTI-IDIOTYPIC ANTIBODIES

This application is a continuation-in-part of application Ser. No. 07/586,207 filed Sep. 21, 1990 now abandoned.

A deposit was made in the American Type Culture Collection, 12301 Parklawn Drive, Rockville, Md. 20852 on Nov. 12, 1992 of the hybridoma cell lines FIP19-1030.2.3.1, FVX38-2814.6 and FVX38-2848.6. The accession numbers for each of the cell lines so deposited are set forth below:

| Cell Line | Accession Number |
| --- | --- |
| FIP19-1030.2.3.1 | HB 11191 |
| FVX38-2814.6 | HB 11192 |
| FVX38-2848.6 | HB 11193 |

BACKGROUND OF THE INVENTION

Various nonspecific serum antibody tests for the diagnosis of feline infectious peritonitis virus (FIPV) are known. These known procedures include the testing of cat sera for immunofluorescent staining of coronavirus infected cell lines. Many of these assays rely upon the antigenic relationship which exists between FIPV and other coronaviruses and utilize either transmissible gastroenteritis virus (TGEV) of swine, canine coronavirus or human respiratory coronavirus. These assays accordingly provide only nonspecific detection of antibody to coronavirus common antigenic determinants. In particular, because of the substantial antigenic similarity between FIPV and feline enteric coronavirus (FeCV), such assays cannot distinguish antibody to FIPV from FeCV.

SUMMARY OF THE INVENTION

There is no known published record of monoclonal antibodies that distinguish FIPV from FeCV nor is there any published report of the application of anti-idiotypic technology to the study of feline antigens.

This invention provides (a) novel hybridoma cell lines which produce a monoclonal idiotypic antibody designated 1030.2.3.1 that binds an antigenic determinant present on FIPV but absent on FeCV; and (b) monoclonal anti-idiotypic antibodies designated 2814.6 and 2848.6 that mimic epitopes of this FIPV specific determinant.

This invention also provides an assay procedure in which such idiotypic and anti-idiotypic monoclonal antibodies are utilized to distinguish antibody to FIPV from FeCV. The invention also includes means including reagents useful to isolate an antigen from FIPV that is not shared by FeCV or to identify specifically the presence of FIPV in a sample that may or may not contain other feline viruses. The monoclonal anti-idiotypic antibodies of the invention are useful to identify antibody to FIPV but not FeCV in a cat's body fluids including, among others, saliva, tears or peritoneal fluid, serum or plasma sample when production of an adequate amount of purified FIPV antigen for this purpose is not feasible.

One embodiment of the invention includes a kit containing the novel monoclonal idiotypic antibody, at least one of the novel anti-idiotypic antibodies and, if desired, other items appropriate for the conduct of an assay pursuant to the invention.

DESCRIPTION OF THE FIGURE

FIG. 1 illustrates discrimination of the assay of this invention between cats infected with FIPV or FeCV.

DETAILED DESCRIPTION OF THE INVENTION

The production of the novel hybridoma cell lines and of the novel monoclonal idiotypic and anti-idiotypic antibodies is described. The procedure for conducting assays or tests for FIPV and the nature of the kits useful to conduct such assays are described.

THE HYBRIDOMA CELL LINES

The novel hybridoma cell lines of the invention were produced by conventional methodologies. See. e.g., Kohler, G. and Milstein, C., "Continuous Cultures of Fused Cells Secreting Antibody of Predefined Specificity, *Nature*, 256:495-497 (1975); Goding, J. W., "Antibody Production by Hybridomas, *J. Immunological Methods.* 39:285-308 (1980); and Bartal, A. H. and Hirshaut, Y., *Methods of Hybridoma Formation,* Humana Press, Clifton, N.J. (1987).

Specifically, Balb/CAF$_1$ mice obtained from Matsunaga Tayman Scientific, San Diego, Calif. (now owned by Harlan Sprague Dawley), were immunized with a series of sub-cutaneous injections of $5 \times 10^6$ FIPV infected *Felis catis* whole fetus (FCWF) cells and 25 ug of polyethylene glycol (PEG) precipitated FIPV. Sera from mice so immunized were monitored by FIPV infected cell ELISA. Spleens from mice were used for fusions to produce hybridomas when a titer of at least 1:51,200, as determined by ELISA, was obtained.

The ELISA used to determine titer of mouse serum was conducted by suspension of FIPV-infected FCWF cells in carbonate buffer to adsorb to microtiter wells overnight. Bovine serum albumin (BSA) was then added to each well in order to block any remaining available sites on the wells. Serial dilutions of mouse serum were incubated in wells for 30 minutes, then washed out. Horseradish peroxidase (HRP) conjugated goat anti-mouse immunoglobulin (Ig) reagent was then added to react with any mouse serum antibody that bound to the FIPV-infected cell material on the wells. Unbound goat anti-mouse Ig-HRP was washed out after 30 minutes of incubation. Lastly, a chromogenic substrate (hydrogen peroxide-ABTS) was added to each well, and optical density readings for each well were obtained with an ELISA plate reader. Normal mouse serum was included in each assay for comparative purposes. Titer, as used in this context, refers to the maximum dilution of serum that gives a positive reaction in the ELISA.

Selected mouse spleen cells were fused with mouse myeloma NS-1, a non-secretor obtained from the American Type Culture Collection (ATCC) (Accession No. TIB18).

The fusion was conducted in the presence of PEG according to standard protocol. See, Goding, supra. The fusion cocktail was distributed to 24 96-well microtiter plates along with normal Balb/C thymocytes to provide initial fusion cultures.

Certain initial fusion cultures were screened by ELISA for antibodies that bind to FIPV. This ELISA procedure was essentially the same as described above for titering mouse sera with minor modifications, i.e., hybridoma culture supernatants were first tested neat (no serial dilutions made), and culture supernatant from an unrelated hybridoma was included in each assay for comparative purposes in place of normal mouse serum. In addition, hybridoma culture supernatants were also checked for cross-reactivity with FeCV, TGEV, CCV, and uninfected FCWF cells.

Three hundred initial cultures were each expanded to 24 well microtitre plates in one (1) ml of thymocyte conditioned medium containing hypoxanthine-aminopterin-thymidine (HAT). Thymocyte-conditioned medium is produced as follows: Mouse thymus glands are aseptically removed and minced in order to disperse thymocytes. Thymocytes are centrifuged and resuspended in Dulbecco's Minimal Essential Medium (DMEM) containing 10% fetal bovine serum (FBS), 2% L-glutamine, and 1% HAT. Thymocytes are then maintained in culture for three days. Prior to use, thymocytes are removed from the conditioned medium by centrifugation.

The expanded cultures were screened by the above-described ELISA. Seven cultures were selected for subcloning to insure monoclonality. The sub-clones were screened by the same ELISA technique. Two subclones from each of the seven selected cultures were expanded, and the expanded subclones were again screened by the same ELISA. One clone, designated 1030.2.3.1 was screened by the same ELISA.

This clone 1030.2.3.1 does not cross react with any of TGEV, FeCV, CCV or FCWF. The tests to determine the absence of such cross-reactivity were conducted in the following manner: Cross-reactivity with FeCV, TGEV, CCV, or uninfected FCWF cells was evaluated with the same ELISA format described above; in place of a suspension of FIPV-infected cells applied to the microtiter wells, the FeCV, TGEV, or CCV-infected cells, or uninfected FCWF cells, were applied to the microtiter wells.

PREPARATION OF ANTI-IDIOTYPIC MONOCLONAL ANTIBODY

Balb/c mice were immunized with a series of intraperitoneal (ip) injections of 50 ug of a conjugate of the idiotypic monoclonal FIPV antibody and KLH and Freund's adjuvant. Sera from the immunized mice were monitored by ELISA for reactivity with the idiotypic monoclonal antibody as follows: A solution of idiotypic antibody in carbonate buffer was adsorbed overnight to microtiter wells, and then the wells were blocked with bovine serum albumin (BSA). Serial dilutions of mouse serum were incubated in wells for 30 minutes, and then washed out. Horseradish peroxidase-conjugated idiotypic antibody was then added to react with any anti-idiotypic antibody that bound to the wells. Unbound idiotypic antibody-HRP was washed out after 30 minutes of incubation. Lastly, a chromogenic substrate (hydrogen peroxide-ABTS) was added to each well, and optical density readings for each well were obtained with an ELISA plate reader. Normal mouse serum was included in each assay for comparative purposes.

Spleen cells from immunized mice, after a titer of at least 1:6400 as determined by ELISA was observed, were fused according to standard protocol (see, Goding, supra) with fast growing mouse myeloma which secreted no immunoglobins (OF myeloma obtained from ATCC (Accession No. CRL1646)). The fusing together of cell membranes of myeloma cells and immunized spleen cells was mediated by polyethylene glycol (PEG) in known manner.

The resulting hybridomas were screened by ELISA to identify antibodies binding to the FIPV idiotype as described above. Specifically:

(i) Initial fusion cultures were tested by ELISA for binding to the Id 1030.2.3.1. 53 positive cultures were identified and expanded.

(ii) The expanded positives from fusion were screened by same ELISA, and 26 cultures with the strongest reactions were selected to be subcloned.

(iii) The subcloned cultures were then tested by the same ELISA, and 160 positive subclones were identified and expanded.

(iv) The expanded clones were tested by the same ELISA and 19 subclones with the strongest reaction were selected to inject into mice for ascites production.

Anti-Ids 2814.6 and 2848.6 were identified as follows: Of the 19 anti-Id subclones injected into mice for ascites production, 17 resulted in the production of ascites fluid. Each of these 17 anti-Id ascites fluids was tested for the ability to compete with authentic FIPV (in the form of FIPV-infected cell material) for binding to the Id 1030.2.3.1 in an ELISA. As shown by Table 1, eight of the 17 anti-Ids competed with authentic FIPV for binding to the Id (Table 1). These eight anti-Ids were designated 2800.3, 2814.6, 2817.6, 2818.7, 2831.5, 2840.1, 2847.8 and 2848.6. The ELISA used to demonstrate this had FIPV-infected cell material (or uninfected cell material) absorbed to the microtiter wells. Mixtures of HRP-conjugated Id 1030.2.3.1 plus each anti-Id were incubated in the wells, the wells were washed, then chromogenic substrate was added. Anti-Ids that competed with authentic FIPV for binding to the HRP-Id resulted in a lower optical density reading than that of HRP-Id added alone to these wells.

TABLE 1

| | α-Ids 1 | 2 | 3 | 4 | O.D. 5 | 6 | 7 | 8 | 9 | α-ids 10 | 11 | 12 | 13 | 14 | 15 | 16 | 17 |
|---|---|---|---|---|---|---|---|---|---|---|---|---|---|---|---|---|---|
| | | | | | | | | Infected Cells | | | | | | | | | |
| A | 0.000 | 0.173 | 0.130 | 0.123 | 0.010 | 0.005 | 0.004 | 0.095 | 0.129 | 0.165 | 0.008 | 0.149 | 0.000 | 0.163 | 0.144 | 0.035 | 0.034 |
| B | 0.009 | 0.156 | 0.150 | 0.131 | 0.008 | 0.007 | 0.006 | 0.122 | 0.163 | 0.169 | 0.009 | 0.145 | 0.035 | 0.172 | 0.157 | 0.038 | 0.035 |
| C | 0.007 | 0.168 | 0.155 | 0.110 | 0.009 | 0.007 | 0.009 | 0.113 | 0.158 | 0.141 | 0.006 | 0.151 | 0.035 | 0.198 | 0.158 | 0.036 | 0.038 |
| D | 0.009 | 0.137 | 0.132 | 0.114 | 0.009 | 0.009 | 0.009 | 0.121 | 0.139 | 0.161 | 0.007 | 0.156 | 0.036 | 0.157 | 0.160 | 0.037 | 0.038 |
| E | 0.010 | 0.134 | 0.131 | 0.117 | 0.008 | 0.005 | 0.011 | 0.111 | 0.141 | 0.117 | 0.012 | 0.136 | 0.040 | 0.206 | 0.161 | 0.039 | 0.037 |
| F | 0.009 | 0.156 | 0.138 | 0.124 | 0.009 | 0.010 | 0.012 | 0.124 | 0.119 | 0.150 | 0.014 | 0.170 | 0.039 | 0.168 | 0.148 | 0.041 | 0.039 |
| G | 0.014 | 0.173 | 0.149 | 0.130 | 0.056 | 0.011 | 0.014 | 0.139 | 0.163 | 0.153 | 0.025 | 0.164 | 0.037 | 0.176 | 0.147 | 0.045 | 0.043 |
| H | 0.015 | 0.175 | 0.155 | 0.201 | 0.051 | 0.011 | 0.018 | 0.126 | 0.168 | 0.131 | 0.027 | 0.194 | 0.053 | 0.164 | 0.148 | 0.046 | 0.041 |
| | | | | | | | | Noninfected Cells | | | | | | | | | |
| A | 0.000 | 0.030 | 0.030 | 0.030 | 0.029 | 0.027 | 0.029 | 0.028 | 0.026 | 0.025 | 0.029 | 0.028 | 0.000 | 0.035 | 0.030 | 0.033 | 0.032 |
| B | 0.030 | 0.031 | 0.032 | 0.030 | 0.030 | 0.029 | 0.029 | 0.025 | 0.027 | 0.209 | 0.029 | 0.026 | 0.033 | 0.033 | 0.032 | 0.032 | 0.029 |
| C | 0.030 | 0.030 | 0.030 | 0.029 | 0.029 | 0.028 | 0.030 | 0.028 | 0.026 | 0.032 | 0.027 | 0.029 | 0.032 | 0.033 | 0.061 | 0.033 | 0.031 |
| D | 0.031 | 0.032 | 0.032 | 0.029 | 0.030 | 0.031 | 0.030 | 0.030 | 0.026 | 0.028 | 0.028 | 0.029 | 0.035 | 0.034 | 0.031 | 0.033 | 0.031 |
| E | 0.030 | 0.031 | 0.033 | 0.031 | 0.029 | 0.039 | 0.033 | 0.027 | 0.029 | 0.027 | 0.030 | 0.026 | 0.035 | 0.032 | 0.031 | 0.031 | 0.033 |

TABLE 1-continued

| α-Ids | | | | O.D. | | | | | α-ids | | | | | | | |
|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 |
| F 0.029 | 0.033 | 0.033 | 0.031 | 0.029 | 0.031 | 0.032 | 0.032 | 0.036 | 0.031 | 0.030 | 0.030 | 0.031 | 0.035 | 0.031 | 0.033 | 0.028 |
| G 0.031 | 0.034 | 0.033 | 0.033 | 0.033 | 0.030 | 0.031 | 0.033 | 0.034 | 0.043 | 0.030 | 0.031 | 0.032 | 0.031 | 0.040 | 0.039 | 0.030 |
| H 0.034 | 0.033 | 0.033 | 0.043 | 0.030 | 0.033 | 0.031 | 0.026 | 0.030 | 0.030 | 0.034 | 0.031 | 0.030 | 0.031 | 0.031 | 0.031 | 0.032 |

α-Ids
1. FVX38-2800.3 (8/07/89)
2. FVX38-2805.5 (8/12/89)
3. FVX38-2806.4 (8/09/89)
4. FVX38-2807.1 (8/14/89)
5. FVX38-2814.6 (8/07/89)
6. FVX38-2817.6 (8/09/89)
7. FVX38-2818.7 (8/10/89)
8. FVX38-2824.8 (8/14/89)
9. FVX38-2825.6 (8/14/89)
10. FVX38-2828.1 (8/14/89)
11. FVX38-2831.5 (8/14/89)
12. FVX38-2832.6 (8/14/89)
13. FVX38-2840.1 (8/07/89)
14. FVX38-2841.7 (8/09/89)
15. FVX38-2844.3 (8/10/89)
16. FVX38-2847.8 (8/10/89)
17. FVX38-2848.6 (8/10/89)
1030.2.3.1-HRP (5/08/89 BR) 1:1600 on plate
Set up = FIPV-infected FCWF cells on microtiter wells.
Each α-Id diluted serially down the plate starting at 1:20 dilution.
Id (1030.2.3.1)-HRP added to all wells (pre-diluted 1:800).
Chromogenic substrate added to all wells.

Table 2 shows that the eight anti-Ids react with serum from FIPV-infected cats, but not with serum from FeCV-infected cats, to varying degrees (Table 2). The ELISA used to demonstrate this had each anti-Id absorbed to microtiter wells, cat sera were incubated in the wells, wells were washed, HRP-conjugated goat anti-cat Ig was added to the wells, wells were washed, and chromogenic substrate was added. Optical density readings were taken.

TABLE 2

| | α-Ids | | | | | |
|---|---|---|---|---|---|---|
| | | | | Optical Density Values | | |
| CATS | 2848.6 | 2814.6 | 2840.1 | 2817.6 | 2818.7 | 2847.6 |
| FIPV+ | 0.107 | 0.092 | 0.090 | 0.064 | 0.154 | 0.087 |
| FIPV+ | 0.102 | 0.115 | 0.098 | 0.064 | 0.178 | 0.057 |
| FeCV+ | 0.048 | 0.046 | 0.038 | 0.031 | 0.049 | 0.044 |

Each of the eight anti-Ids was conjugated to horseradish peroxidase (HRP). Mixtures were made of each of the eight HRP-conjugated anti-Ids with each of the eight unconjugated anti-Ids. These mixtures, as well as each HRP-conjugated anti-Id alone, were incubated in microtiter wells coated with the Id 1030.2.3.1. Wells were washed; then chromogenic substrate was added. Anti-Ids were deemed to react with the same, or very close, idiotypic determinant if the optical density obtained for the HRP-conjugated and unconjugated anti-Ids was less than that for the unconjugated anti-Id alone. In this way, it was determined that seven of the eight anti-Ids recognized the same idiotypic determinant, and one anti-Id (2848.6) did not compete with any of the other seven anti-Ids. 2848.6 was selected for use in the diagnostic assay because of its unique specificity. It has been determined, however that 2848.6 may cause some non-specific binding with some cat samples. 2814.6 was selected because its reaction with the Id was the strongest of the other seven anti-Ids.

THE ASSAY PROCEDURE AND KIT

The assay of the invention may be performed in microtiter plate wells coated with a solution that contains at least one and preferably at least two different anti-idiotypic monoclonal antibodies each specific for FIPV, for example, the antibodies secreted by the hybridoma cell lines 2814.6 and 2848.6. Antibody 2814.6 is preferred. Feline body fluid samples e.g., serum or plasma samples, preferably after dilution with phosphate buffered saline which may contain serum proteins, and a detergent are incubated in the coated wells to permit serum or plasma antibody to FIPV to bind to the anti-idiotypes. The wells are then thoroughly rinsed to remove unbound serum or plasma antibody and/or other elements. An enzyme labelled anti-cat antibody reagent, e.g., polyclonal antisera to cat antibody, is then incubated in the same wells. The wells are again rinsed and an enzyme substrate and chromogen are added. A positive reaction is indicated by development of color beyond that observed for a negative control reaction run in independent wells. A positive control reaction is also run and confirms the integrity of the assay components. In some cases, samples that react specifically with mouse immunoglobulin may result in false positives. Such false positives may be avoided by supplementing the sample diluent with irrelevant mouse immunoglobulin to absorb this non-specific reactivity. Irrelevant mouse immunoglobulin may also be added to the polyclonal detect antibody.

The test can be set up in other formats such as dipsticks, tubes, beads or membranes in lieu of microtiter plates as the solid phase. The test or assay may also be conducted in the liquid phase with conventional means of capturing and demonstrating the final anti-idiotypic-/antibody reaction. For example, anti-Ids bound to inert particles (such as latex, agarose) are mixed with a cat serum or plasma sample and allowed to react. This mixture is then passed through a membrane filter with a pore size that will not allow the anti-Id-beads to pass through. The membrane filter could then be reacted with enzyme-conjugated anti-cat Ig reagent, followed by addition of a chromogenic substrate. This will detect any cat Id that bound to the anti-Id beads.

Kit components useful in the practice of the invention may be microtiter plates having anti-idiotypic FIPV monoclonal antibody coated wells, a sample diluent such as phosphate-buffered saline containing serum proteins and detergent, an HRP anti-cat antibody conjugate, a positive control, e.g., Id 1030.2.3.1, conjugated to HRP, a negative control like unrelated monoclonal antibody conjugated to HRP, urea peroxide solution (the substrate for HRP), and TMB, which is the chromogen that indicates the presence of the peroxidase-peroxide reaction.

Cat sera useful in conjunction with the kit components include FIP(+) cat sera, FeCV cat sera and healthy (−) sera pool. A protocol for use with such a kit follows:

1. Dilute cat sera 1:40 in wells by adding two drops of sample diluent, preferably containing irrelevant mouse immunoglobulin, and 1 microliter of cat sera. This is done in duplicate. Into additional wells, add 1 drop of Positive Control and 1 drop of Negative Control. Tap sides of plate to mix. Incubate 20 minutes at room temperature.
2. Dump and wash wells 4× with saline.
3. Add 1 drop/well of conjugate. Tap sides of plate. Incubate 20 minutes a room temperature.
4. Add 1 drop/well of Urea Peroxide Solution. Add 1 drop/well of TMB Solution. Tap sides of plate to mix. Read plate at 5 min. and 10 min. at dual wavelength: L1=650 nm; L2=490 nm.

Table 3 reports data obtained by use of such a kit and protocol.

TABLE 3

|  | Positive Control | Negative Control | FIP+ | FIP− FeCV+ | Healthy FIP−, FeCV− |
|---|---|---|---|---|---|
| Test 1 | Blue | No color | Blue | No color | No color |
| Test 2 | Blue | No color | Blue | No color | No color |
| Test 3 | Blue | No color | Blue | No color | No color |
| Test 4 | Blue | No color | Blue | No color | No color |

The utility of this assay procedure has been demonstrated in clinical trials in which known FIPV-infected cat samples were positive in this assay and known FeCV-infected cat samples were negative. Approximately 400 samples from normal cats were tested as well; 98% of these were negative in this assay. The remaining 2% might represent cats that were exposed to FIPV at some time, and developed an antibody response to the virus, but were not infected.

DISCRIMINATION BETWEEN CATS INFECTED WITH FIPV OR FeCV

Specific pathogen-free, laboratory cats were experimentally infected with either FIPV or FeCV, and serum samples collected from these cats were tested in the assay of this invention. Sera obtained from confirmed cases of FIP in the field were tested as well. The ability of this assay to discriminate between cats infected with FIPV or FeCV is demonstrated in FIG. 1. This is significant because the methods currently available for detecting antibody to FIPV do not make this distinction. As a result, feline practitioners have been unable to distinguish infections by FIPV from infections by other feline coronaviruses.

We claim:
1. The hybridoma cell line 1030.2.3.1 or 2814.6 or 2848.6.
2. A monoclonal antibody secreted by the hybridoma cell line 1030.2.3.1, or 2814.6 or 2848.6.
3. A conjugate of an enzyme and the monoclonal antibody secreted by the hybridoma cell line 1030.2.3.1.
4. A conjugate as defined by claim 3 in which the enzyme is horseradish peroxidase.

5. A kit useful for distinguishing between infection by feline infectious peritonitis virus (FIPV), and feline enteric coronavirus (FeCV), which comprises:
   (i) a solid phase bearing the monoclonal antibody secreted by the hybridoma cell line 2814.6; and
   (ii) as a positive control, the monoclonal antibody secreted by the hybridoma cell line 1030.2.3.1.
6. A kit useful for distinguishing between infection by FIPV and FeCV which comprises:
   (i) a solid phase bearing two different anti-idiotypic monoclonal antibodies secreted by the hybridoma cell lines 2814.6 and 2848.6, each specific for FIPV; and
   (ii) a positive control idiotypic monoclonal antibody that binds to an antigenic determinant present on FIPV but absent on FeCV.
7. A kit as defined by claim 6 in which said idiotypic monoclonal antibody is secreted by the hybridoma cell line 1030.2.3.1.
8. A kit as defined by claim 6, further comprising a sample diluent, a negative control, an enzyme substrate and a chromogen.
9. A kit as defined by claim 6 in which said solid phase is a microtiter plate, a dipstick, a tube, a bead or a membrane.
10. A solid surface bearing an anti-idiotypic monoclonal antibody secreted by a hybridoma cell line 2814.6 or 2848.6.
11. An assay useful to distinguish between infection by FIPV and FeCV which comprises:
   (i) incubating feline body fluid in contact with a solid phase,
      said solid phase bearing an anti-idiotypic monoclonal antibody secreted by a hybridoma cell line 2814.6 or 2848.6,
   (ii) thereafter removing unbound body fluid from said solid surface, and
   (iii) determining whether or not an anti-cat antibody reagent binds to said solid surface, wherein binding of anti-cat antibody reagent to said solid surface indicates infection with FIPV.
12. An assay as defined by claim 11 in which said body fluid is serum or plasma.
13. An assay as defined by claim 11 or 12 in which said solid phase is a microtiter plate.
14. An assay as defined by claim 11 or claim 12 or claim 13 in which there is utilized in step (i) a solid surface bearing two different anti-idiotypic monoclonal antibodies secreted by the hybridoma cell lines 2814.6 and 2848.6.
15. An assay useful to distinguish between infection by FIPV and FeCV which comprises:
   (i) incubating feline serum, plasma, saliva, tears, or peritoneal fluid in contact with a solid phase,
      said solid phase bearing at least one anti-idiotypic monoclonal antibody secreted by a hybridoma cell line 2814.6 or 2848.6,
   (ii) removing unbound sample,
   (iii) thereafter incubating said solid phase with an enzyme-labelled anti-cat antibody, and
   (iv) determining whether or not said enzyme-labelled anti-cat antibody is bound to said solid phase, wherein the presence of bound labelled anti-cat antibody is an indication of FIPV infection.
16. An assay as defined by claim 15 in which there is utilized in step (i) a solid phase bearing two different anti-idiotypic monoclonal antibodies, said two different antibodies being secreted by the hybridoma cell ines 2814.6 and 2848.6.

17. An assay useful to distinguish between infection by FIPV and FeCV which comprises:

(i) incubating feline physiological specimen in contact with a solid phase, said solid phase bearing one anti-idiotypic monoclonal antibody which mimics the FIPV epitope bound by the monoclonal antibody secreted by the hybridoma cell line 1030.2.3.1, (ii) thereafter removing the unbound physiological specimen from said solid surface, and (iii) determining whether said anti-idiotypic monoclonal antibody, binds to said solid surface, wherein such binding is an indication of 18. A monoclonal antibody secreted by the hybridoma cell line 1030.2.3.1 that binds to an antigenic determinant present on feline infectious peritonitis virus but absent on feline enteric coronavirus.

19. A monoclonal anti-idiotypic antibody secreted by the hybridoma cell line 2814.6 or 2848.6 that mimics an epitope of an antigenic determinant present on feline infectious peritonitis virus but not on feline enteric coronavirus.

20. A kit useful for distinguising between infection by feline infectious peritonitis virus and feline enteric coronavirus, said kit comprising a sample diluent, a negative control, and a monoclonal antibody as defined by claim 18.

21. A method for diagnosing FIPV infection in a susceptible host which comprises:

(i) obtaining a physiological specimen from said host, which specimen contains FIPV or FeCV, and (ii) determining the presence of antibodies to FIPV in said physiological specimen by reaction with an anti-idiotypic antibody which is secreted by the hybridoma cell line 2814.6 or 2848.6

* * * * *